US010632318B2

United States Patent
Stouffer

(10) Patent No.: US 10,632,318 B2
(45) Date of Patent: Apr. 28, 2020

(54) EXTERNAL CHARGER WITH THREE-AXIS MAGNETIC FIELD SENSOR TO DETERMINE IMPLANTABLE MEDICAL DEVICE POSITION

(71) Applicant: Boston Scientific Neuromodulation Corporation, Valencia, CA (US)

(72) Inventor: Thomas W. Stouffer, Chatsworth, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 321 days.

(21) Appl. No.: 15/889,656

(22) Filed: Feb. 6, 2018

(65) Prior Publication Data
US 2018/0272139 A1 Sep. 27, 2018

Related U.S. Application Data

(60) Provisional application No. 62/474,491, filed on Mar. 21, 2017.

(51) Int. Cl.
| | |
|---|---|
| *H01M 10/46* | (2006.01) |
| *A61N 1/378* | (2006.01) |
| *H02J 50/90* | (2016.01) |
| *H02J 7/02* | (2016.01) |
| *A61N 1/372* | (2006.01) |
| *A61N 1/36* | (2006.01) |

(Continued)

(52) U.S. Cl.
CPC ....... *A61N 1/3787* (2013.01); *A61N 1/37235* (2013.01); *A61N 1/37247* (2013.01); *H02J 7/025* (2013.01); *H02J 50/90* (2016.02); *A61B 2034/2051* (2016.02); *A61N 1/05* (2013.01); *A61N 1/362* (2013.01); *A61N 1/3605* (2013.01)

(58) Field of Classification Search
USPC .......................................... 320/107, 108, 114
See application file for complete search history.

(56) References Cited

U.S. PATENT DOCUMENTS

| | | | |
|---|---|---|---|
| 5,314,453 | A | 5/1994 | Jeutter |
| 5,948,006 | A | 9/1999 | Mann |

(Continued)

OTHER PUBLICATIONS

Innternational Search Report and Written Opinion regarding corresponding PCT Application No. PCT/US2018/017218, dated May 17, 2018.

*Primary Examiner* — Edward Tso
(74) *Attorney, Agent, or Firm* — Lewis & Reese, PLLC

(57) ABSTRACT

An external charger for an implantable medical device (IMD) is disclosed including a three-axis magnetic field sensor at the center of a primary charging coil. The sensor first senses a magnetic charging field produced by the coil with no IMD present (vector A). The sensor then senses the field in useful operation when such field is being provided to the IMD (vector B). From these vectors, a vector C is calculated representing the magnetic field reflected from the IMD. Vector C can be used to determine a vector D, representing the position of the IMD in physical space relative to the external charger. Information comprising one or more volumes can be stored in the external charger, and compared with vector D to determine whether charger-to-IMD positioning will provide an adequate amount of power to the IMD, and/or to provide an indication of charger-to-IMD alignment.

18 Claims, 6 Drawing Sheets

(51) Int. Cl.
*A61N 1/362* (2006.01)
*A61B 34/20* (2016.01)
*A61N 1/05* (2006.01)

(56) References Cited

U.S. PATENT DOCUMENTS

| | | | |
|---|---|---|---|
| 5,973,611 | A | 10/1999 | Kulha et al. |
| 6,138,681 | A | 10/2000 | Chen et al. |
| 6,298,271 | B1 | 10/2001 | Weijand |
| 6,510,345 | B1 | 1/2003 | Van Bentem |
| 6,516,227 | B1 | 2/2003 | Meadows et al. |
| 7,177,698 | B2 | 2/2007 | Klosterman et al. |
| 7,191,013 | B1 | 3/2007 | Miranda et al. |
| 7,225,032 | B2 | 5/2007 | Schmeling et al. |
| 7,486,048 | B2 | 2/2009 | Tsukamoto et al. |
| 7,650,192 | B2 | 1/2010 | Wahlstrand |
| 7,774,069 | B2 | 8/2010 | Olson et al. |
| 7,932,696 | B2 | 4/2011 | Peterson |
| 8,140,168 | B2 | 3/2012 | Olson et al. |
| 8,214,042 | B2 | 7/2012 | Ozawa et al. |
| 8,260,432 | B2 | 9/2012 | DiGiore et al. |
| 8,311,638 | B2 | 11/2012 | Aghassian |
| 8,321,029 | B2 | 11/2012 | Aghassian |
| 8,335,569 | B2 | 12/2012 | Aghassian |
| 8,401,663 | B2 | 3/2013 | Aghassian |
| 8,463,392 | B2 | 6/2013 | Aghassian |
| 8,473,066 | B2 | 6/2013 | Aghassian et al. |
| 8,498,716 | B2 | 7/2013 | Chen et al. |
| 8,554,322 | B2 | 10/2013 | Olson et al. |
| 8,626,297 | B2 | 1/2014 | Jaax et al. |
| 8,666,491 | B2 | 3/2014 | Chen et al. |
| 8,682,444 | B2 | 3/2014 | Aghassian et al. |
| 8,744,592 | B2 | 6/2014 | Carbunaru et al. |
| 8,886,333 | B2 | 11/2014 | Lui et al. |
| 8,942,935 | B2 | 1/2015 | Michaels et al. |
| 9,002,445 | B2 | 4/2015 | Chen |
| 9,030,159 | B2 | 5/2015 | Chen et al. |
| 9,031,665 | B2 | 5/2015 | Aghassian |
| 9,031,666 | B2 | 5/2015 | Fell |
| 9,186,520 | B2 | 11/2015 | Aghassian |
| 9,211,418 | B2 | 12/2015 | Aghassian |
| 9,227,075 | B2 | 1/2016 | Aghassian et al. |
| 9,314,642 | B2 | 4/2016 | Ozawa et al. |
| 9,339,660 | B2 | 5/2016 | Feldman et al. |
| 9,356,473 | B2 | 5/2016 | Ghovanloo |
| 9,867,994 | B2 | 1/2018 | Parramon |
| 2002/0055763 | A1 | 5/2002 | Zarinetchi et al. |
| 2003/0085684 | A1 | 5/2003 | Tsukamoto et al. |
| 2004/0230247 | A1 | 11/2004 | Stein et al. |
| 2006/0227989 | A1 | 10/2006 | Polinske |
| 2007/0060980 | A1 | 3/2007 | Strother et al. |
| 2007/0103617 | A1 | 5/2007 | Kitajima et al. |
| 2007/0255176 | A1* | 11/2007 | Rondoni ............... A61B 5/202 600/573 |
| 2008/0027293 | A1 | 1/2008 | Vodermayer et al. |
| 2008/0027513 | A1 | 1/2008 | Carbunaru |
| 2008/0046034 | A1 | 2/2008 | Ibrahim |
| 2009/0082835 | A1 | 3/2009 | Jaax et al. |
| 2009/0112291 | A1 | 4/2009 | Wahlstrand et al. |
| 2009/0216068 | A1 | 8/2009 | Thomas et al. |
| 2009/0259273 | A1 | 10/2009 | Figueiredo et al. |
| 2010/0331917 | A1 | 12/2010 | DiGiore et al. |
| 2010/0331918 | A1 | 12/2010 | DiGiore et al. |
| 2010/0331919 | A1 | 12/2010 | DiGiore et al. |
| 2011/0004278 | A1 | 1/2011 | Aghassian et al. |
| 2011/0270134 | A1* | 11/2011 | Skelton ............. A61N 1/36514 600/595 |
| 2011/0276111 | A1 | 11/2011 | Carbunaru et al. |
| 2011/0301667 | A1 | 12/2011 | Olson et al. |
| 2012/0012630 | A1 | 1/2012 | Lui et al. |
| 2012/0197322 | A1* | 8/2012 | Skelton ................ A61N 1/3787 607/2 |
| 2012/0277831 | A1 | 11/2012 | Joshi |
| 2013/0009665 | A1 | 1/2013 | Clerc et al. |
| 2013/0023958 | A1 | 1/2013 | Fell |
| 2013/0096651 | A1 | 4/2013 | Ozawa et al. |
| 2014/0114373 | A1 | 4/2014 | Aghassian |
| 2014/0324126 | A1 | 10/2014 | Ozawa |
| 2014/0354211 | A1 | 12/2014 | Zottola et al. |
| 2015/0028798 | A1 | 1/2015 | Dearden et al. |
| 2015/0073498 | A1 | 3/2015 | Kothandaraman |
| 2016/0096028 | A1 | 4/2016 | Aghassian |
| 2016/0126771 | A1 | 5/2016 | Aghassian et al. |
| 2016/0263385 | A1 | 9/2016 | Aghassian |
| 2016/0301239 | A1 | 10/2016 | Funderburk |
| 2017/0151440 | A1 | 6/2017 | Parramon et al. |
| 2017/0214268 | A1 | 7/2017 | Howard |
| 2017/0214269 | A1 | 7/2017 | Howard |
| 2017/0361113 | A1 | 12/2017 | Aghassian et al. |

* cited by examiner

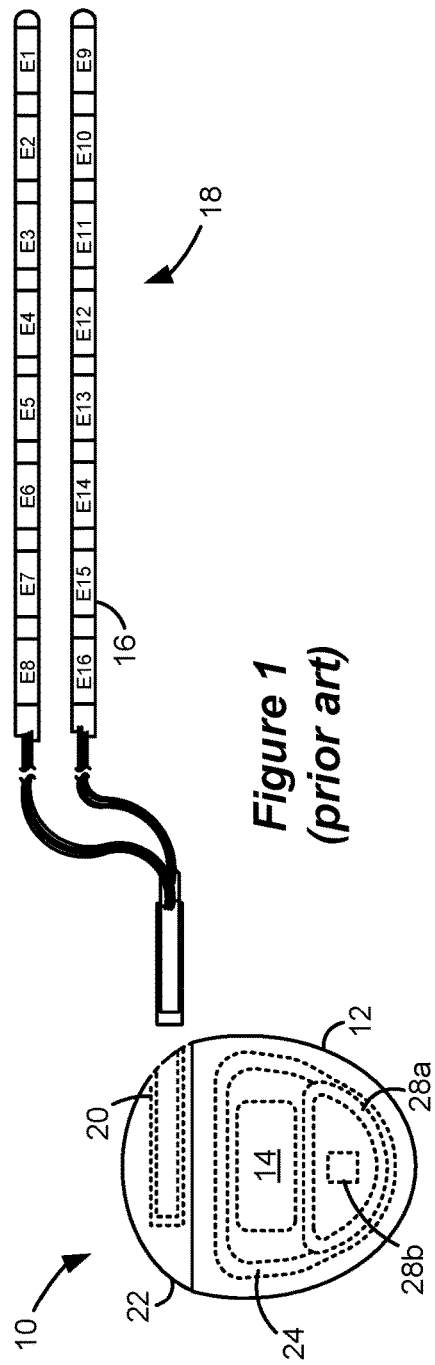
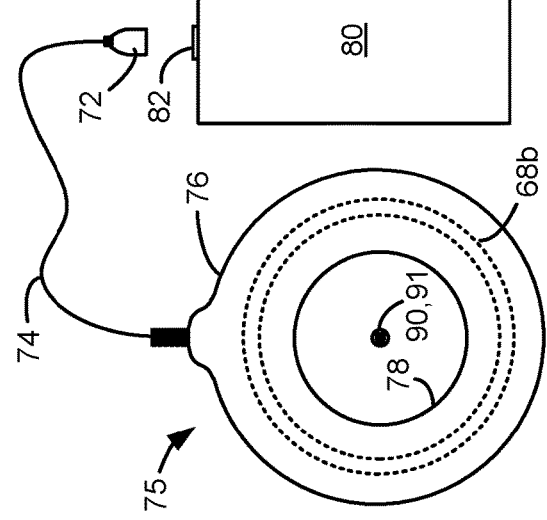
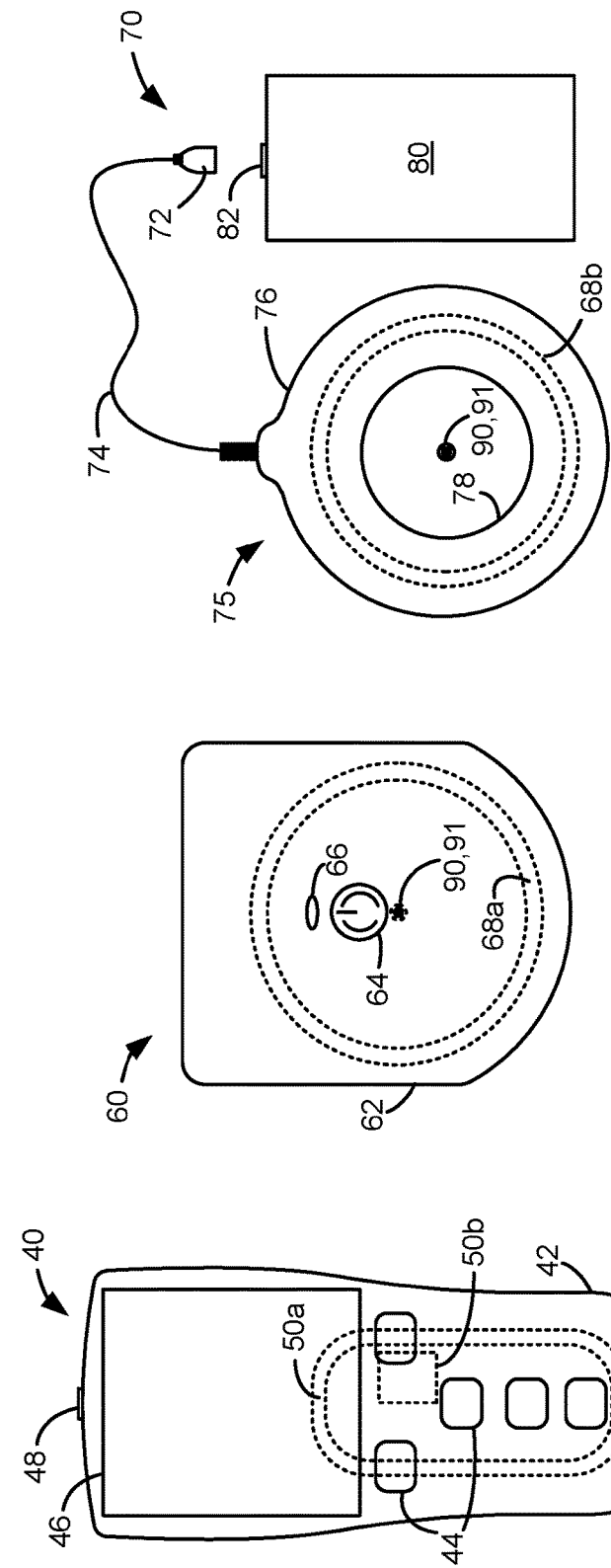

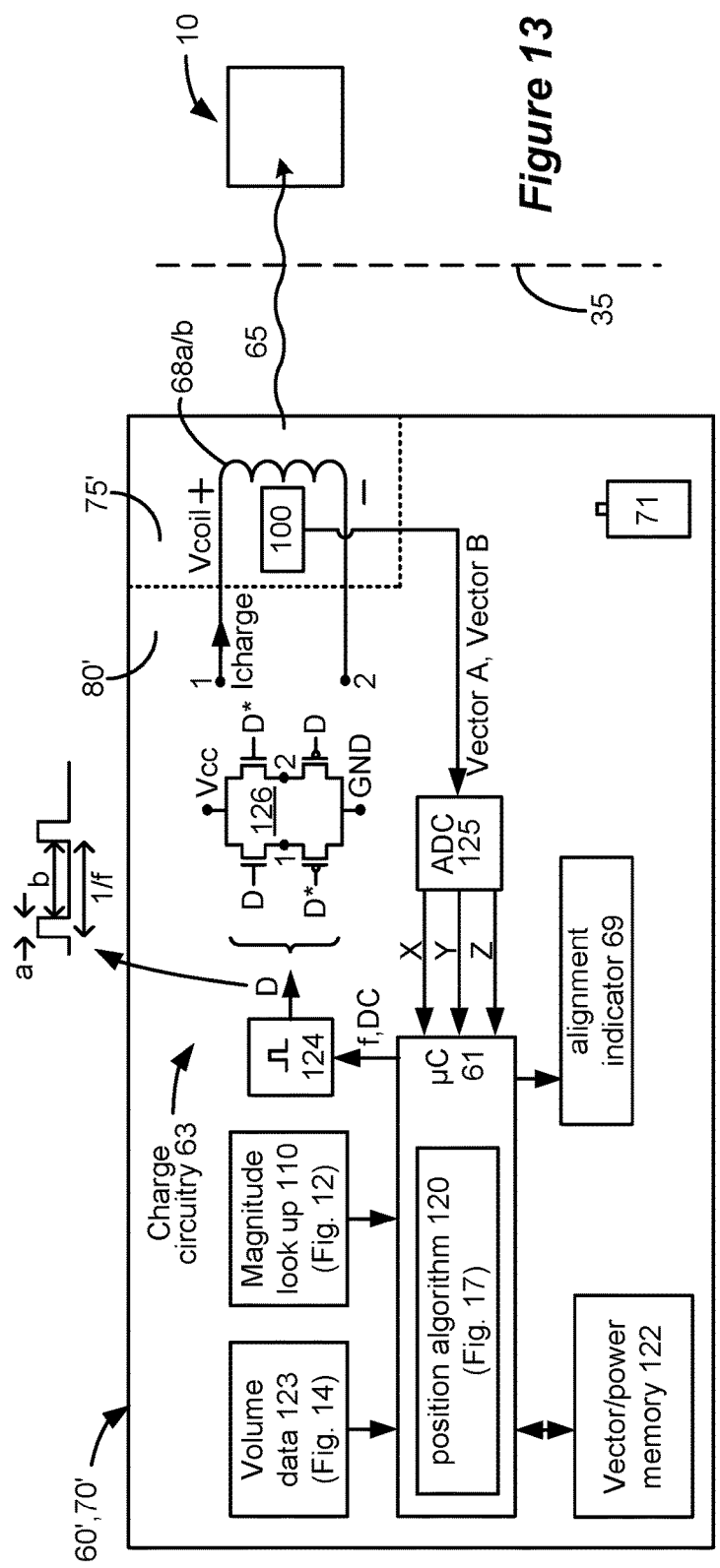
*Figure 13*
*Figure 14*
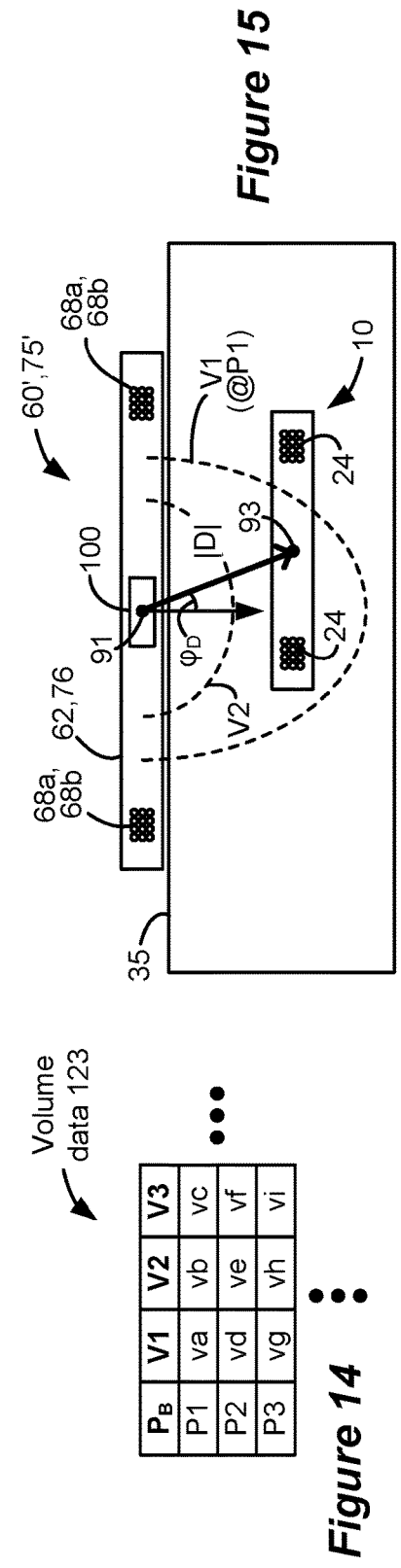
*Figure 15*

EXTERNAL CHARGER WITH THREE-AXIS MAGNETIC FIELD SENSOR TO DETERMINE IMPLANTABLE MEDICAL DEVICE POSITION

CROSS REFERENCE TO RELATED APPLICATIONS

This is a non-provisional application based on U.S. Provisional Patent Application Ser. No. 62/474,491, filed Mar. 21, 2017, which is incorporated herein by reference, and to which priority is claimed.

FIELD OF THE TECHNOLOGY

The present disclosure relates to an external charging system for an implantable medical device.

INTRODUCTION

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators (DBS) to treat motor and psychological disorders, and other neural stimulators to treat urinary incontinence, sleep apnea, shoulder subluxation, etc. The description that follows will generally focus on the use of the technology within a spinal cord stimulation (SCS) system, such as that disclosed in U.S. Pat. No. 6,516,227. However, the present disclosure may find applicability with any implantable medical device (IMD) or in any IMD system.

As shown in FIG. 1, a SCS system includes an Implantable Pulse Generator (IPG) 10 (hereinafter, and more generically, IMD 10), which includes a biocompatible device case 12 formed of titanium for example. The case 12 typically holds the circuitry and battery 14 necessary for the IMD 10 to function. The IMD 10 is coupled to electrodes 16 via one or more electrode leads 18 (two of which are shown). The proximal ends of the leads 18 are coupled to the IMD 10 at one or more lead connectors 20 fixed in a header 22, which can comprise an epoxy for example. There are sixteen electrodes (E1-E16) in the illustrated example, although the number of leads and electrodes is application specific and therefore can vary. In an SCS application, two electrode leads 18 are typically implanted on the right and left side of the dura within the patient's spinal column. The proximal ends of the leads 18 are then tunneled through the patient's tissue 35 (FIG. 6) to a distant location, such as the buttocks where the IMD case 12 is typically implanted, at which point they are coupled to the lead connectors 20.

An IMD 10 is typically supported by and communicates with one or more external devices, and FIGS. 2 and 3 provide examples of such devices. FIG. 2 depicts an external controller 40 for the IMD 10. The external controller 40 is used to establish a bi-directional wireless data link with the IMD 10, and is typically used to send or adjust the therapy settings the IMD 10 will provide to the patient. If the IMD 10 is an IPG 10 as depicted in FIG. 1, such therapy settings may include which electrodes 16 are active to issue therapeutic current pulses; whether such electrodes sink or source current (i.e., electrode polarity); the duration, frequency, and amplitude of the pulses, etc., which settings together comprise a stimulation program for the IMD 10. External controller 40 can also act as a receiver of data from the IMD 10, such as various data reporting on the IMD's status and the level of the IMD's battery 14.

As shown in FIG. 2, external controller 40 typically comprises a hand-held, portable housing 42, and is powered by an internal battery (not shown). The external controller 40 includes a Graphical User Interface (GUI) similar to that used for a cell phone, including buttons 44 and a screen 46, and may have other interface aspects as well, such as a speaker. While an external controller 40 is typically a device custom built by the manufacturer of the IMD 10 and dedicated in its functionality to IMD communications, external controller 40 may also comprise a general purpose, freely programmable mobile device having suitable wireless communication functionality, such as a smart cell phone. In this case, a Medical Device Application (MDA) can be executed on the mobile device to configure the device's GUI for use as an IMD external controller, and to allow for control and monitoring of the IMD 10. See, e.g., U.S. Patent Application Publication 2015/0073498. External controller 40 may include a port 48, such as a USB or other customized port.

Both the external controller 40 and IMD 10 have antennas to effectuate the bi-directional data communication link, and such antennas can come in different forms and operate pursuant to different protocols or communication standards. In one example, both these devices can includes coil antennas, with IMD 10 including an antenna coil 28a inside its case 12, and external controller 40 including an antenna coil 50a inside its housing 42. Such antennas, which may comprise a plurality of turns of wire, may communicate by near-field magnetic induction, as is well known. The IMD 10 and external controller 40 may also include radio-frequency (RF) antennas 28b and 50b (e.g., Bluetooth antennas), which communicate by far-field electromagnetic waves, and which may comprise wires, slots, or patches for example. Although shown inside the case 12, the IMD 10's data antenna 28a or 28b can also be located in its header 22.

FIG. 3 depicts an external charger 60 for an IMD 10, see U.S. Patent Application Publication 2013/0096651, which is used to recharge the IMD 10's rechargeable battery 14 or to provide continuous power to the IMD 10 should it lack a battery. This preferably occurs by near-field magnetic induction, and FIG. 5 shows an example of the circuitry involved. Charging circuitry 63, under control of control circuitry 61 (e.g., a microcontroller) and using power from a battery 71, energizes a primary charging coil 68a with an AC current (Icharge) of a frequency preferably in the range of 10 MHz or less. This produces an AC magnetic charging field 65 with this same frequency, which field passes through the patient's tissue 35 and induces a current in the IMD 10's secondary charging coil 24. The induced AC current is rectified to a DC level (Vdc) by rectifier circuitry 23, which may comprise for example a single diode, or a half- or full-wave rectifier. Vdc can then be used to charge the IMD battery 14 or to provide continuous power to the IMD (load) if it lacks a battery, perhaps through charging and protection circuitry 25 as an intermediary. Control circuitry 21 (e.g., a microcontroller) can monitor charging, e.g., Ibat or Vbat, as well as control the main functionality of the IMD 10.

Referring again to FIG. 3, the user interface of the external charger 60 may be simple compared to the external controller 40. For example, the external charger 60 may lack a screen. Instead, the external charger 60 may simply include an on/off button 64 for magnetic charging field 65 generation, and a light emitting diode (LED) 66 to indicate when the magnetic field is being generated. External charger 60 may also include an alignment indicator 69 (FIG. 5) useful to indicate alignment between the external charger and the IMD 10, discussed further below and discussed in the above-referenced '651 Publication. External charger 60 is also typically hand-held and portable, with its electrical components, including the primary charging coil 68a, integrated within a housing 62. External charger 60 may additionally include IMD data-communication abilities, and may effectively comprise a charger and controller 40 combined into a single housing, as disclosed in U.S. Pat. No. 8,335,569 for example. The center 91 of the primary charging coil 68a and the axis 90 that runs through it are explained further below with reference to FIG. 6.

FIG. 4 shows another external charger 70 that may be used to charge IMD 10, which is disclosed for example in U.S. Pat. Nos. 8,498,716, 8,463,392, and U.S. Patent Application Publication 2017/0361113. This external charger 70 includes a charging coil assembly 75, which includes a primary charging coil 68b within a housing 76. The charging coil assembly 75 couples to a charging controller 80 via a cable 74, for example, using a connector 72 on the cable and a port 82 on the charging controller. Cable 74 can also be hardwired to the charging controller 80. Although not shown, the charging controller 80 includes a user interface to allow a patient to charge his IMD 10—i.e., to produce a magnetic charging field 65 from primary charging coil 68b similar to the manner described above—and may also allow data relevant to IMD charging to be indicated. The charging controller 80 may comprise a device specifically dedicated to charging functionality, as disclosed in U.S. Patent Application Publication 2007/0060980. Alternatively, the charging controller 80 may comprise the external controller 40 described earlier (FIG. 2), in which case the charging controller 80 would include charging functionality in addition to data-communication functionality. External charger 70 may otherwise function similarly to the external charger 60 as described earlier. Circuitry shown in FIG. 5 will preferably reside within the charging controller 80 leaving only the primary charging coil 68b within the housing 76 of the charging coil assembly 75, although portions of such circuitry can also reside within housing 76. As shown, a hole 78 may be present in the housing 76 of the assembly 75 in the center of the primary charging coil 68b, or the housing may lack a hole and thus be disk shaped.

FIG. 6 shows external charger 60 (FIG. 3) or charging coil assembly 75 (FIG. 4) and IMD 10 in cross section, such that primary charging coil 68a or 68b and secondary charging coil 24 in the IMD 10 can be seen. Centers in these devices can be defined as relevant to charging. As shown, center 91 is defined as the center of primary charging coil 68a/68b, and center 93 is defined as the center of secondary charging coil 24, which centers may be located in the plane in which their respective coils are wound. If coils 68a/68b or 24 are not perfectly circular, centers 91 and 93 may comprise other generally central points, such as a geometric centroid of the coils 68a/68b or 24. Center 91 may also be defined as a point where the magnetic charging field 65 generated by the primary charging coil 68a/68b is strongest, and center 93 may also be defined as a point where largest amount of magnetic flux passes through secondary charging coil 24. Centers 91 and 93 may also comprise central points in or on the external charger 60 or charging coil assembly 75, and the IMD 10. For the IMD 10 in particular, the conductive case 12 or other conductive structures in the IMD 10 such as the battery 14 may affect the receipt of the magnetic charging field 65 in a manner that would more logically define center 93 at a location that is not necessarily at the center of its secondary charging coil 24. Despite these various manners in which centers 91 and 93 may be defined, subsequent figures assume that centers 91 and 93 are at the centers of circular charging coils 68a/68b and 24.

It is preferable that the external charger 60 or charging coil assembly 75 (particularly their primary charging coils 68a or 68b) be well aligned with the IMD 10 (particularly secondary charging coil 24). Stated differently, primary charging coil 68a/68b and secondary charging coil 24 should be well coupled, such that a high amount of the power input to the primary charging coil 68a/68b is received at the secondary charging coil 24. If there is good alignment, charging of the IMD 10 will be most efficient—i.e., take the least amount of time, or require the least amount of power input to the primary charging coil 68a/68b. Good alignment is achieved if axis 90 through center 91 is collinear with a similar axis 92 through center 93 of the IMD 10's secondary charging coil 24.

An example of good alignment is shown in FIG. 6 as position I. If axes 90 and 92 are laterally misaligned, as shown in position J, coupling between the coils 68a/68b and 24 may be poor: charging will either be slow; or the power input to primary charging coils 68a/68b must be increased to charge at the same rate as when the IMD is in position I. As the above-referenced patent documents explain, external chargers such as 60 and 70 can monitor for misalignment, and indicate misalignment to the patient via alignment indicator 69. Such indication may come in the form of a beeping sound to alert the patient that he must try to laterally move his external charger 60 or the external charging coil assembly 75 into better alignment with the IMD 10; if realignment is successful this indication will cease. Alignment indicator 69 may take other forms, such as forms visible by the patient, including screens, LEDs, etc. Alignment indicator 69 may also indicate a relative degree of alignment or coupling rather than providing a binary determination of alignment or misalignment, such as by use of a multi-bar indicator. See, e.g., U.S. Pat. No. 7,932,696.

Indicating misalignment in an external charger system is a useful feature. Even though holding devices can be used to hold an external charger 60 or external charging coil assembly 75 against a patient (or his clothing) and in good initial alignment with the IMD 10 (position I) during a charging session, see U.S. Patent Application Ser. No. 62/458,295, filed Feb. 13, 2017, movement by the patient can cause the external charger 60 or external charging coil assembly 75 to shift away from the IMD 10 (position J).

Distance t between the planes of the primary charging coil 68a/68b and the secondary charging coil 24 can, like alignment, also affect coupling, with larger distances resulting in poorer coupling, and hence lower power receipt at the secondary charging coil 24. Such distance t is normally a set variable for a given patient, because the IMD 10 has been implanted at a particular depth in the patient's tissue 35. Hence, the secondary charging coil 24 at a shallow position I for one patient will receive a higher amount of power from the primary charging coil 68a/68b than would a secondary charging coil at a deeper position K for another patient. Note that adjustment of lateral alignment of the primary charging coil 68a/68b outside the tissue 35 may not help improve coupling to a deep IMD 10: the axes 90 and 92 may be collinear and hence the charging coil 68a/68b may already in the best alignment with the secondary charging coil 24, even if coupling is poor.

The effect of relative positioning between the primary charging coil 68a/68b and the secondary charging coil 24 can be understood with reference to volume V1, which is bounded by a dashed line in FIG. 6 and defined relative to the center 91 of the primary charging coil 68a/68b. If the IMD 10—for example, the center 93 of its secondary charging coil 24—is within volume V1, the secondary charging coil 24 is considered well coupled to the primary charging coil 68a/68b, and hence will receive a suitable amount of power for the IMD 10. The boundary of volume V1 can be defined with regard to a parameter indicative of IMD power receipt. For example, the boundary of volume V1 may be defined by IMD 10 positions in which the charging current received by the battery 14 in the IMD 10, Ibat (FIG. 5), equals a minimum desired amplitude, such as 50 mA. IMD 10 positions inside this boundary (e.g., position I) will result in even better coupling, and thus higher battery charging currents (Ibat>50 mA) and faster charging rates, while IMD 10 positions outside of this boundary (positions J and K) will result in lower coupling, lower battery charging currents (Ibat<50 mA) and slower charging rates.

Volume V1 is 3-dimensional, and is generally radially symmetric relative to axis 90 if charging coil 68a/68b is also radially symmetric to this axis. For example, the boundary of volume V1 may be generally paraboloid in shape. Note that volume V1 is further defined at a particular power level (e.g., P1) for the magnetic charging field 65. If the power of the magnetic charging field 65 is increased, then volume V1 would increase in size as well because a larger range of IMD 10 positions would now receive the minimum desired amplitude of Ibat. Reducing the power would likewise shrink the size of volume V1.

A number of volumes may exist, each indicating different degrees of coupling. For example, FIG. 6 shows another volume V2 within volume V1, whose boundary may be defined as IMD positions where the battery charging current Ibat equals a higher value, such as 75 mA. Therefore, an IMD 10 position within volume V2 will have even higher battery charging currents, with Ibat>75 mA. An IMD 10 position between the boundaries of volumes V1 and V2 will result in a battery charging current between 50 mA and 75 mA. Another parameter that can define the degree of coupling to the IMD, and hence can be used to define the one or more volumes V1, V2, is the voltage of the charging coil, Vcoil. See the above-referenced '651 Publication.

BRIEF DESCRIPTION OF THE DRAWINGS

FIG. 1 shows an implantable pulse generator (IPG) type of implantable medical device (IMD), in accordance with the prior art.

FIGS. 2 and 3 show external devices for an IMD, including an external controller (FIG. 2) and an integrated external charger (FIG. 3), in accordance with the prior art.

FIG. 4 shows an external charger for an IMD having a charging controller and a charging coil assembly connected by a cable, in accordance with the prior art.

FIG. 11 shows example values for vectors A, B, C, and D.

FIG. 13 shows improved circuitry in the external charger, including a position algorithm, for measuring and calculating the various vectors and assisting in the charging process.

FIG. 14 shows volume data stored in the external charger, which volume data associates the physical position between the external charger and IMD with their coupling.

FIG. 15 shows comparison of vector D to the volume data, as useful to determine the coupling between the external charger and the IMD.

DETAILED DESCRIPTION

Figure 5:
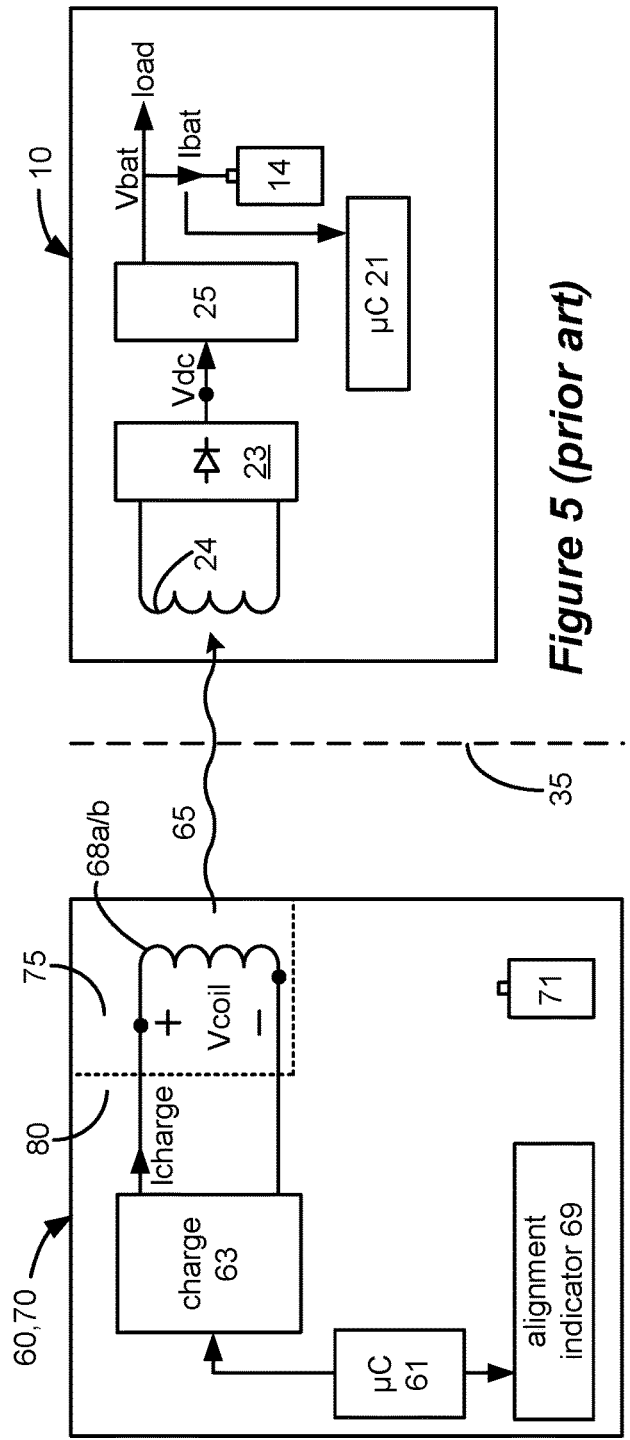
FIG. 5 shows circuitry involved in generation of a magnetic charging field at the external charger, and circuitry involved in receipt of the magnetic charging field at the IMD, in accordance with the prior art.
Figure 6:
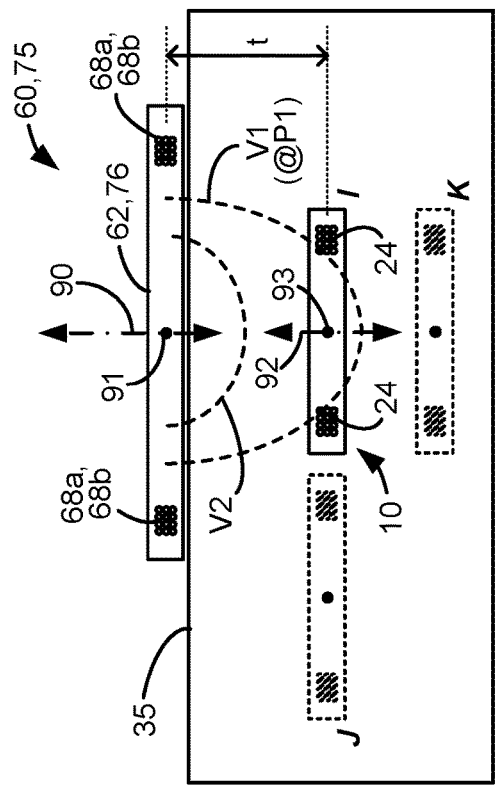
FIG. 6 shows in cross section the charging coils in an external charger and the IMD, and shows different positions of the external charger relative to the IMD, in accordance with the prior art.

The inventor is concerned that the external chargers 60 or 70 described earlier lack the ability to discern the relative position of an IMD 10 they are charging, that is, the position of the IMD 10 relative to the primary charging coil 68a/b in three-dimensional space. This has important implications because, as discussed further below, an external charger would preferably take different actions if it is laterally misaligned with respect to an IMD 10 as shown in position J of FIG. 6, or if it is generally aligned but deeply implanted in a patient as shown in position K.

The inventor addresses such concerns by providing an improved external charger, which may comprise an improved integrated external charger 60' similar in form factor to the integrated external charger 60 described earlier (FIG. 3), or an improved external charger 70' similar in form factor to the external charger 70 described earlier (FIG. 4) having an improved charging controller 80' and an improved charging coil assembly 75'. Note that external chargers 60' and 70' can be constructed similarly to external chargers 60 and 70, and can contain much of the same components and perform much of the same functionality as described earlier. Such details are not reiterated, and instead the following focuses on componentry and functionality that is new in external chargers 60' and 70'.

By way of introduction, the improved external charger includes a three-axis magnetic field sensor 100 preferably at the center of the primary charging coil 68a/68b and able to detect the magnitude of magnetic fields in X, Y, and Z dimensions. Preferably, the sensor 100 first senses the magnetic charging field 65 with no IMD 10 present as initialization vector A. The sensor 100 then senses the magnetic charging field 65 in useful operation when such field is being provided to an IMD 10 as vector B, which comprises the sum of the magnetic charging field 65 and any magnetic field reflected from the IMD 10. From these vectors, a vector C is calculated which represents the magnetic field reflected from the IMD 10. Vector C can be used to determine a vector D, representing the position of the IMD 10 in physical space relative to the external charger, and relative to the primary charging coil 68a/68b in particular. Information comprising one or more volumes can be stored in the external charger, and compared with vector D to determine whether charger-to-IMD positioning will provide an adequate amount of power to the IMD, or to determine the amount of that power. Vector D can also be used to provide an indication whether the charger is laterally aligned or misaligned with the IMD 10, and also if desired the direction of misalignment. Finally, vector D can be used to adjust the strength of the magnetic charging field 65.

Figure 7:
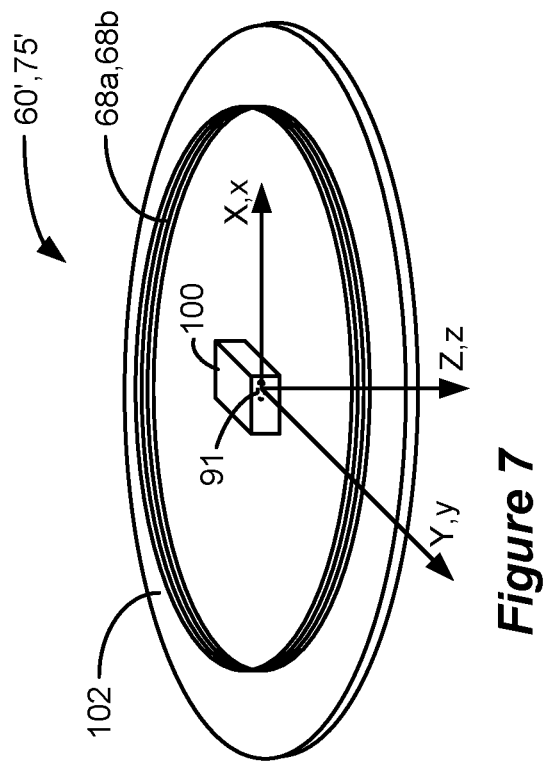
FIG. 7 shows an improved external charger having a three-axis magnetic field sensor at the center of its primary charging coil.

Starting with FIG. 7, the improved external charger 60' or assembly 75' of external charger 70' is shown (with housings 62/76 removed), including a three-axis magnetic field sensor 100, which as just noted is preferably located at the center 91 of external charger 60' or at the center 91 of the primary charging coil 68b of the charging coil assembly 75' of external charger 70'. Sensor 100 can take different forms, and can comprise different types magnetic sensing elements, such as orthogonally-oriented coils (e.g., Part No. 3DC09LP, manufactured by Premo, S.L.), magneto-resistive elements (e.g., Part No. HMC1053, manufactured by Honeywell Microelectronics & Precision Sensors), or Hall Effect elements (e.g., A1363LLUTR-1-T, manufactured by Allegro MicroSystems, LLC). Sensor 100 is preferably integrated in a single package, but can also comprise three separate orthogonally-mounted magnetic field sensors, each capable of sensing a magnetic field in a single direction.

Support and electrical connection to the three-axis magnetic field sensor 100 is provided by a circuit board 102. In examples in which the sensor 100 is provided in an external charging coil assembly 75', no hole 78 would be present (compare FIG. 4) as the circuit board 102 preferably covers the center of the assembly, and housing 76 of the assembly 75' would be disk shaped. In the example shown, both the primary charging coil 68a/68b and the sensor 100 are provided on a top surface of the circuit board 102 relative to the IMD 10 being charged, but this is not necessary and either or both of these components could be provided on the bottom surface of the circuit board 102.

FIG. 7 also illustrates two different three-dimensional coordinate systems whose origin like three-axis magnetic field sensor 100 appears at center 91 of the primary charging coil 68a/68b. A first coordinate system defined by orthogonal axes X, Y, and Z describes the magnetic field strengths that are present in orthogonal directions. This first coordinate system is relevant to vectors A, B, and C described below. A second coordinate system defined by orthogonal axes x, y, and z describes distance in three-dimensional physical space. This second coordinate system is relevant to vector D described below. The illustrated three-dimensional coordinate systems and vectors within them can be Cartesian or Spherical, or converted between the two, as explained further below.

Figure 8:
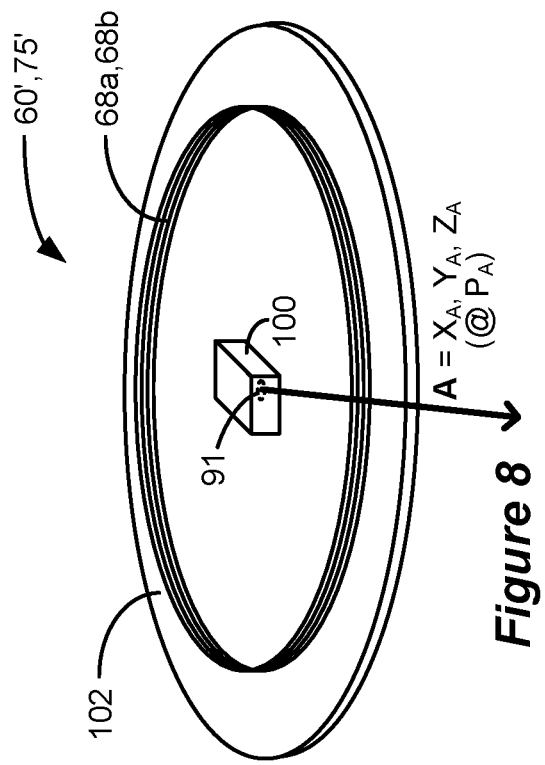
FIG. 8 shows use of the three-axis magnetic field sensor to measure a vector A indicative of the strength of a magnetic charging field when no IMD is proximate to the charger.

FIG. 8 shows use of the three-axis magnetic field sensor 100 to measure an initialization vector A, which is measured while the primary charging coil 68a/68b is generating a magnetic charging field 65 when the IMD 10 is not present, i.e., when the IMD 10 is not proximate to the external charger 60' or charging coil assembly 75'. Vector A is represented by three Cartesian X, Y, and Z coordinates ($X_A$, $Y_A$, and $Z_A$) which represent the peak magnitudes detected by each of the axial sensors in the sensor 100. Relevant circuitry in the external charger 60' or 70' is shown in FIG. 13, including an Analog-to-Digital converter (ADC) 125 that receives the output of the sensor 100 and determines and provides coordinates $X_A$, $Y_A$, and $Z_A$ to the control circuitry 61 (e.g., a microcontroller). ADC 125 preferably samples quickly enough relative to the AC frequency of the magnetic charging field 65 to identify the peak magnitudes of the magnetic charging field 65 in the three axial directions. Although shown separately, ADC 125 may comprise part of the sensor 100, or part of the charger's control circuitry 61 should that control circuitry be capable of receiving analog inputs.

Vector A is preferably measured during manufacturing of the external charger 60' or 70', and is useful to account for variations that occur during manufacturing of the external charger. In an ideal case, the magnetic charging field 65 would be perfectly perpendicular to the plane of the primary charging coil 68a/68b, and hence $X_A$ and $Y_A$ would equal zero. However, due to non-idealities—such as imperfect placement or planarity of the three-axis magnetic field sensor 100, variation in the uniformity or thickness of the windings of the primary charging coil 68a/68b, interference caused by conductive components in the external charger, etc.—$X_A$ and $Y_A$ may have small values. FIG. 8 shows such non-ideality, as vector A is not illustrated as perfectly perpendicular.

Referring again to FIG. 13, one measured, vector A is preferably stored in memory 122 in the external charger 60' or 70', along with a representation of the power $P_A$ of the magnetic charging field 65 used while vector A was measured. Memory 122 can comprise part of control circuitry 61 or can be an external memory accessible to the control circuitry 61.

Also shown in FIG. 13 are further details of one example of the charging circuitry 63 that can be used to energize the charging coil 68a/68b with AC current, Icharge. In this example, a digital drive signal D is formed by a square wave generator 124, which may comprise part of the control circuitry 61. Drive signal D comprises a pulse-width modulated (PWM) signal with a periodically-repeating portion that is high (logic '1') for a time portion 'a' and low for a time portion 'b'. As such, the drive signal D has a duty cycle DC equal to a/(a+b), and a frequency f equal to 1/(a+b), which duty cycle and/or frequency can be specified by the control circuitry 61. The frequency f of the drive signal D is generally set to or near the resonant frequency of the primary charging coil 68a/68b (e.g., 10 MHz or less). A capacitor (not shown) may be provided in parallel or in series with the primary charging coil 68a/68b to establish an LC tank circuit with a particular resonant frequency.

Charging circuitry 63 can further include a well-known H-bridge configuration, including two P-channel transistors coupled to a power supply voltage Vcc, and two N-channel transistors coupled to a reference potential such as ground (GND). The transistors are driven on and off by the drive signal D and its logical complement D*. In so doing, the power supply voltage Vcc and ground alternate across the primary charging coil 68a/68b at frequency f, thus producing the magnetic charging field 65 at this frequency. Power supply voltage Vcc may comprise the voltage of the battery 71 or may be regulated from that voltage. As is well known, the duty cycle DC of the drive signal D can be increased from 0 to 50% to increase Icharge, thus affecting the power at which the primary charging coil 68a/68b is energized and hence the power of the resulting magnetic field 65.

Thus, the duty cycle of drive signal D can comprises a representation of the power $P_A$ of the magnetic charging field 65 used while producing vector A, and thus the duty cycle can be stored in memory 122 along with vector A. If duty cycle doesn't scale linearly with magnetic charging field 65 power, control circuitry 61 may convert the duty cycle to an actual power value before power $P_A$ is stored in memory 122. Other representations of power $P_A$ may also be used and stored with vector A. For example, peak values for Icharge, Vcoil, or their product, can also be used, and thus well-known measuring circuitry (not shown) may be provided in the external charger 60' or 70' to determine such parameters.

Figure 9:
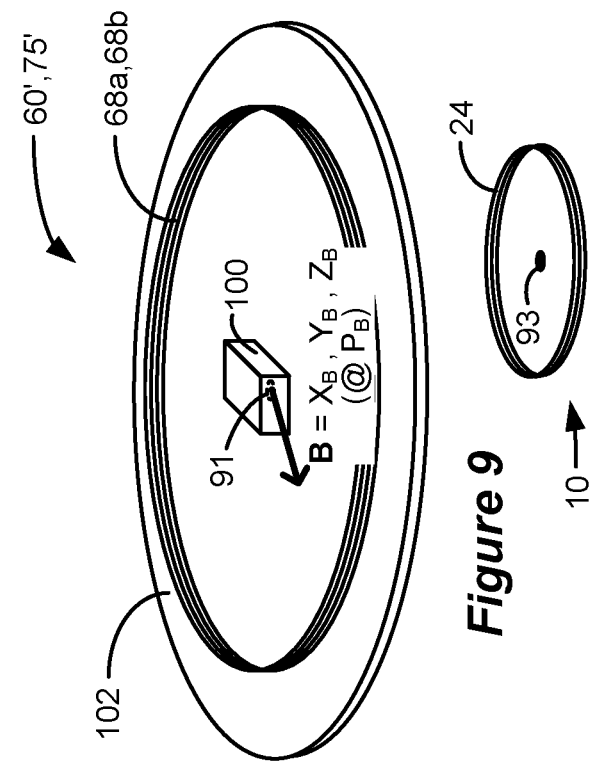
FIG. 9 shows a similar measurement of a vector B when the IMD is receiving a magnetic charging field during normal use of the charger.

FIG. 9 shows the external charger 60' or 70' in actual use when primary charging coil 68a/68b is providing a magnetic charging field 65 to an IMD 10. Also shown is a new vector B ($X_B$, $Y_B$, $Z_B$) that is measured by the three-axis magnetic field sensor 100. When the IMD 10 is coupled to and receives power from the magnetic charging field 65, induced currents in the IMD 10 (primarily in the IMD's secondary charging coil 24, but in other conductive structures in the IMD as well including the conductive case 12) will form an opposing or "reflected" magnetic field. As such, measured vector B comprises the superposition of magnetic charging field 65 and this reflected magnetic field from the IMD 10. Vector B, like vector A, preferably comprises the peak magnitudes detected by each of the axial sensors in the sensor 100.

The power $P_B$ of the magnetic charging field 65 when vector B is being measured may not necessarily equal the power $P_A$ used during initialization to measure vector A. This is because during actual operation of external charger 60' or 70', the strength of the magnetic charging field 65 may change for other well-known reasons—such as to control the temperature of the external charger 60' or 70' or the IMD 10. Like power $P_A$, power $P_B$ may be represented by the duty cycle currently being used by the charging circuitry 63 to produce the magnetic charging field 65, or by other parameters (Icharge, Vcoil, etc.). Vector B and its power representation $P_B$ are preferably stored in memory 122, and again the control circuitry 61 may convert such parameters to an actual power value prior to storage.

Figure 10:
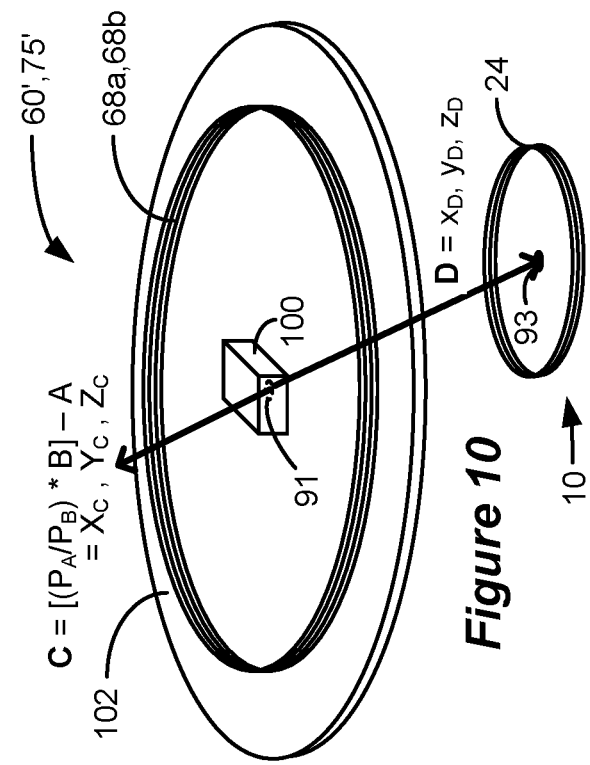
FIG. 10 shows a vector C calculated using vectors A and B, which vector C indicates the magnitude and direction of the magnetic charging field reflected from the IMD.

FIG. 10 shows a vector C calculated using vectors A and B. To calculate vector C, vector B is preferably normalized to the power $P_A$ at which vector A was measured (($P_A/P_B$) *B). Vector A is then subtracted from this normalized vector B ([($P_A/P_B$)*B]−A) to arrive at vector C. Vector C thus represents the reflected magnetic field from the IMD 10 as centered at center 91, and assuming vector B was measured at the same power as vector A (i.e., assuming $P_B$ equals $P_A$). In the example of FIG. 10, vector C is defined in a manner that points directly away from the IMD 10, but vector C may also be defined to point towards the IMD 10 by reversing the subtraction (e.g., C=A−[($P_A/P_B$)*B]). In either case, because vectors A and B are both measured by the same three-axis magnetic field sensor 100, both vectors are affected by the same manufacturing non-idealities discussed earlier, and therefore subtraction of vector A and (normalized) vector B cancels such non-idealities from vector C. As such, vector C is free of manufacturing variance, and accurately indicates the position of the IMD 10 relative to the center 91 of the primary charging coil 68a/68b.

Figures 11, 12:
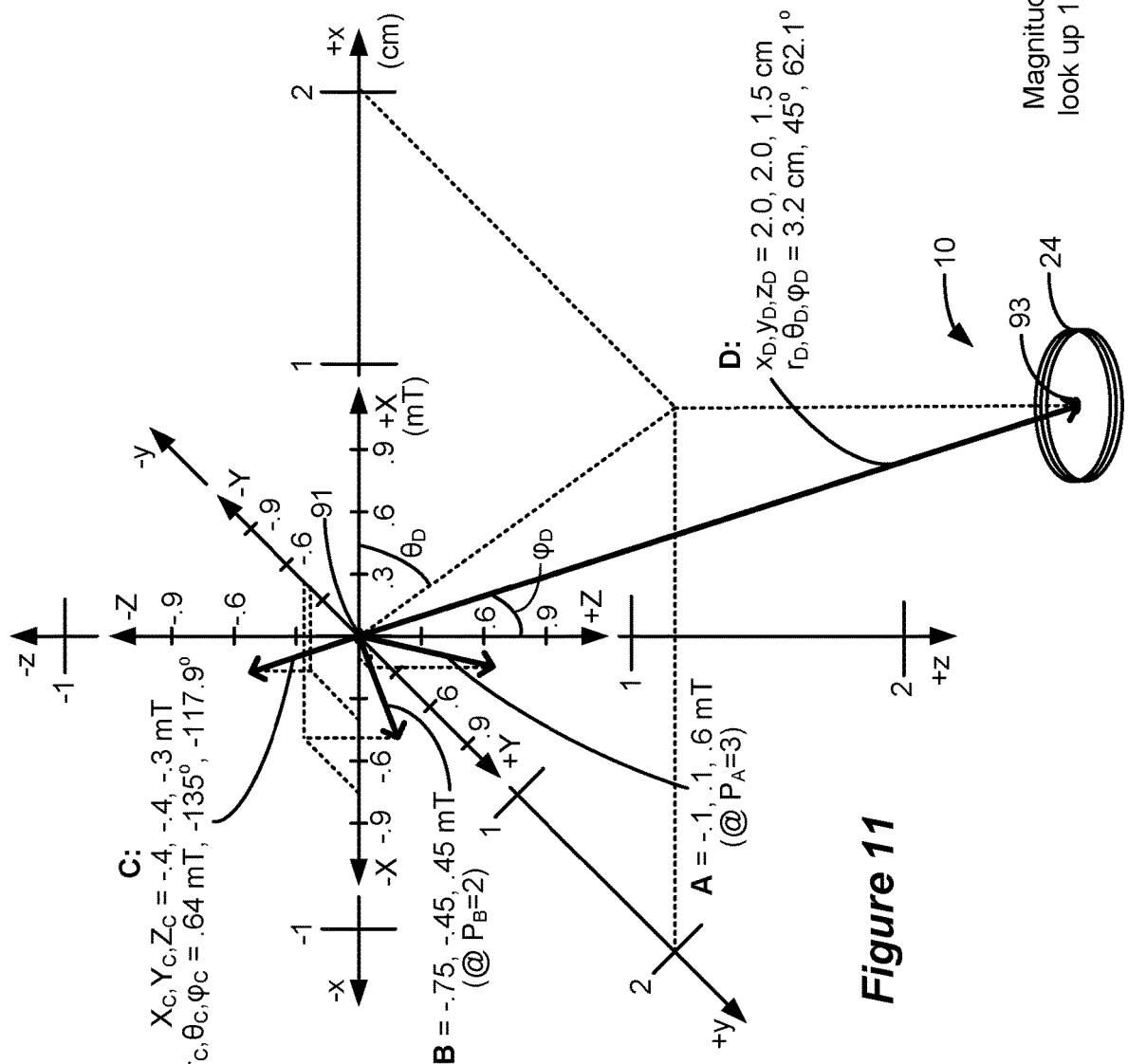
FIG. 11 further shows a vector D calculated form vector C, which points to the IMD in physical space.
FIG. 12 shows a look up table stored in the external charger and used to determine the magnitude of vector D.

FIG. 11 shows the calculation of vector C using example values for vectors A and B. In this example, initialization vector A was measured at a relative power of 3, and its coordinates $X_A$, $Y_A$, $Z_A$ as reported from three-axis magnetic field sensor 100 are −0.1, 0.1, 0.6 milliTesla (mT). Vector B when IMD 10 is present is measured at a relative power of 2, and its coordinates $X_B$, $Y_B$, and $Z_B$ are reported as −0.75, −0.45, 0.45 mT. Vector B, when normalized to vector A's power ($P_A/P_B$=2/3), has coordinates −0.5, −0.3, 0.3 mT. Calculated vector C comprises normalized vector B minus vector A, and therefore has coordinates $X_C$, $Y_C$, and $Z_C$ of −0.5−(−0.1), −0.3−0.1, 0.3−0.6, or −0.4, −0.4, −0.3 mT.

Vectors A, B, and C as noted earlier are defined in coordinate system X, Y, and Z, denoting magnetic field strength, which is represented in FIG. 11 in milliTeslas as one example of a general order of magnitude. However, it is useful in determining the position of the IMD 10 relative to the external charger 60' or 70' (or its primary charging coil 68a/68b more precisely) to determine a vector D in coordinate system x, y, and z, denoting physical space in centimeters for example.

Because vector C comprises the magnetic field reflected from the IMD 10, vector D will point in the opposite direction as vector C (as illustrated in FIG. 11), or in the same direction as vector C (depending on how vector C is defined, as explained above). In either case, the direction of vector D can be determined from the direction of vector C, and in this regard it can be useful to convert vector C (e.g., −0.4, −0.4, −0.3) into spherical coordinates ($r_C$, $\theta_C$, $\varphi_C$=0.64 mT, −135°, −117.9°), where $r_C$ equals vector's C's magnitude (|C|=SQRT($X_C^2+Y_C^2+Z_C^2$)), and where $\theta_C$, $\varphi_C$ describe vector's C direction, with $\theta_C$ denoting the polar angle relative to the +X axis in the X-Y plane, and $\varphi_C$ denoting the azimuthal angle relative to the +Z axis.

The direction $\theta_D$, $\varphi_D$ of vector D can be determined from the direction $\theta_C$, $\varphi_C$ of vector C, and direction $\theta_D$, $\varphi_D$ may either equal $\theta_C$, $\varphi_C$, or (as illustrated) comprise these angles plus 180 degrees (again, depending on how vector C is defined). Given the example values of vector C in FIG. 11, vector D's direction can be calculated as polar angle $\theta_D$=45° relative to the +x axis in the x-y plane, and azimuthal angle $\varphi_D$=62.1° relative to the +z axis.

Vector D's magnitude (|D|=$r_D$) can be determined with the assistance of a magnitude look up table 110, as shown in FIG. 12 and as stored in the external charger 60' or 70' (FIG. 13). Look up table 110 preferably uses both the magnitude of calculated vector C (|C|=$r_C$) and azimuthal angle $\varphi_D$ from the z axis, to determine magnitude |D|=$r_D$, because these parameters have significant effect on magnitude |D|=$r_D$ as explained further below. Look up table 110 can be determined in different manners, but is preferably determined empirically by experimentation. For example, the manufacturer of the external charger 60' or 70' can place the IMD 10 at different known positions ($r_D$, $\theta_D$, $\varphi_D$) relative to the charging coil 68a/68b, measure vector B, calculate vector C (which is normalized to vector A's power as described above), thus giving the manufacturer all information needed to populate the table 110.

Radial symmetry of the charging system with respect to axis 90 through center 91 (see FIG. 6) means that polar angle $\theta_D$ shouldn't significantly affect magnitude |D|=$r_D$, and hence this value is not included in look up table 110 as relevant to determining magnitude |D|=$r_D$. Magnitude |C|=$r_C$ however will affect |D|=$r_D$: a larger reflected magnetic field magnitude |C|=$r_C$ will mean that the IMD 10 is closer to the charging coil 68a/68b (e.g., to its center 91). Hence, |D|=$r_D$ will be inversely proportional to |C|=$r_C$. Azimuthal angle $\varphi_D$ is also relevant to determining magnitude |D|=$r_D$: at a given magnitude for vector D, the magnitude of the reflected magnetic field |C|=$r_C$ will be larger if the IMD 10 is well aligned with the charging coil 68a/68b (e.g., if $\varphi_D$=0°) due to good coupling to the IMD 10's secondary charging coil 24. By contrast, at that same magnitude for vector D, the magnitude of the reflected magnetic field |C|=$r_C$ will be smaller if the IMD 10 is poorly aligned with the charging coil 68a/68b (e.g., as $\varphi_D$ approaches 90°) due to poor coupling.

Once the magnitude $|C|=r_C$ is determined, and azimuthal angle $\varphi_D$ is determined using vector C as described above, the magnitude $|D|=r_D$ can be determined from the look up table 110, and magnitude $|C|=r_C$ and azimuthal angle $\varphi_D$ can be represented in table 110 as ranges to assist in the look up procedure. For example, the magnitude of vector C in the example of FIG. 11 is $|C|=r_C=0.62$ mT, corresponding to range c2-c3 in table 110. Azimuthal angle $\varphi_D$ as already noted is 62.1°, corresponding to angle range 60-70° in the table 110. This yields from the look up table 110 a magnitude $|D|=r_D=3.20$ cm. Because angle $\theta_D$ was also previously calculated (45°), all Spherical coordinates for vector D in physical space are known: $D=r_D, \theta_D, \varphi_D=3.2$ cm, 45°, 62.1°, which can be converted back to Cartesian coordinates $D=x_D, y_D, x_D=2.0, 2.0, 1.5$ cm. While use of a look up table 110 is a convenient manner of establishing the magnitude of vector D, other means can be used. For example, magnitude D could also be determined using equations.

Using the described process, the position of the IMD 10 relative to the charging coil 68a/68b in three-dimensional space has been determined as vector D. In the figures, vector D is shown as pointing to the center 93 of the secondary charging coil 24. However, this may not be accurate, especially given, as discussed above, that other conductive structures in the IMD 10 will affect the reflected magnetic field from the IMD 10 upon which vector D is based. Still, representing vector D as pointing to center 93 in the figures is convenient and reasonable.

Vector D is preferably determined continuously (e.g., every 0.5 seconds) during an IMD 10 charging session, and can be used in different manners to assist in the charging process. In one example, data indicative of the degree of coupling to the IMD, such as one or more volumes V1, V2 as described earlier (see FIG. 6), can be stored in memory 123 in the external charger 60' or 70' (FIGS. 13, 14), which may can comprise part of control circuitry 61 or can be an external memory accessible to the control circuitry 61. Such data may represent three-dimensional representations of the boundary of such volume(s). As noted earlier, the size of volumes V1, V2 are dependent on the power of the magnetic charging field, and so it is convenient to store volumes in memory 123 in the form of a table, associating various magnetic field powers as used during charging (e.g., $P_B$, as represented for example by duty cycle) with the one or more volumes V1, V2.

FIG. 15 shows comparison of vector D to volumes V1, V2 as retrieved from volume memory 123 to determine coupling, and hence whether the IMD 10 is receiving an acceptable amount of power from the magnetic charging field 65. In this example, charging is occurring at power $P_B$=P1, and so the relevant volume data (e.g., V1=va, V2=vb, etc.) has been retrieved from memory 123 (FIG. 14). In this example, the magnitude of vector D ($|D|$) and its azimuthal angle $\varphi_D$ show that the IMD 10 (e.g., the center 93 of its secondary charging coil 24) is within volume V1, which indicates to the control circuitry 61 that the IMD 10 is receiving an acceptable amount of power—for example, that the charging current provided to IMD battery 14 is at least Ibat=50 mA. Comparisons to other volume data (e.g., volume V2) stored in memory 123 would provide even further resolution regarding coupling and the power that the IMD 10 is receiving. For example, if vector D ($|D|$ and $\varphi_D$) points outside of volume V1, then Ibat<50 mA; if between volumes V1 and V2, then 50 mA<Ibat<75 mA; etc.

Depending on this comparison of vector D to the one or more volumes V1, V2, the external charger 60' or 70' may take various actions. For example, if vector D indicates an IMD position outside of an acceptable charging volume (e.g., V1), the external charger 60' or 70' may indicate poor coupling to the patient via alignment indicator 69 (e.g., by beeping), or may indicate the degree of coupling, for example using a multi-bar indicator as described earlier. Such indication may come regardless of the reason for poor coupling—i.e., either because the charging coil 68a/68b is laterally misaligned with the IMD (e.g., position J in FIG. 6), or because the IMD 10 is implanted deeply in the patient (e.g., position K).

Alternatively, the external charger 60' or 70' may use vector D to determine the reason for poor coupling—lateral misalignment or a deep implantation—and only indicate lateral misalignment to the patient. This is sensible, because as mentioned earlier a patient may not be able to adjust external charger positioning to improve coupling to a deeply implanted IMD 10. In this regard, azimuthal angle $\varphi_D$ can be used to additionally determine whether to indicate misalignment. For example, if coupling is poor, i.e., vector D points outside of volume V1, and the azimuthal angle $\varphi_D$ is large (e.g., 20°<$\varphi_D$<90°), alignment indicator 69 may issue, because such a large angle suggests a significant lateral misalignment between the charging coil 68a/68b and the IMD 10, which suggests that repositioning the charging coil 68a/68b might be useful to improve coupling. By contrast, if coupling is poor, and the azimuthal angle is small (e.g. 0°<$\varphi_D$<20°), there is already reasonable lateral alignment between the charging coil 68a/68b and the IMD 10, which suggests that repositioning the charging coil 68a/68b is unlikely to improve coupling. In this circumstance, poor coupling is related to deep implantation of the IMD 10, and it may therefore not be warranted to issue an indication from the alignment indicator 69 because the patient will be unable to effectively address this indication.

Alternatively, or additionally, the external charger 60' or 70' may adjust the strength of the magnetic charging field 65. For example, if vector D points outside of volume V1, indicating poor coupling, the external charger 60' may increase the power (e.g., the duty cycle) of the magnetic charging field—e.g., from $P_B$=P1 to $P_B$=P2. As noted earlier, this will increase the size of volume V1, and therefore making it more likely that the IMD 10 will receive adequate power—i.e., that vector D will now point inside of volume V1. Note that adjusting the power $P_B$ during charging should not affect the magnitude or position of vector D: adjusting the power will scale the magnitude of vector B as measured by three-axis magnetic field sensor 100, but this magnitude is normalized to initialization vector before deriving vector C, which is also then normalized to vector A. Vector D is then derived from vector C, and so vector D's magnitude and direction should remain unaffected by the change in power. Even though magnetic charging field 65 power can be increased to provide more power to a poorly coupled implant, one skilled will realize that there may be other factors (e.g., temperature) that may make it unwise or impossible to do so at a given point in time. Further, depending on the comparison of vector D to one or more volumes V1, V2, and if coupling is higher than needed, the power of the magnetic charging field 65 can also be reduced, which may assist in reducing system temperatures, and save on battery (71) power in the external charger 60' or 70'.

Figure 16:
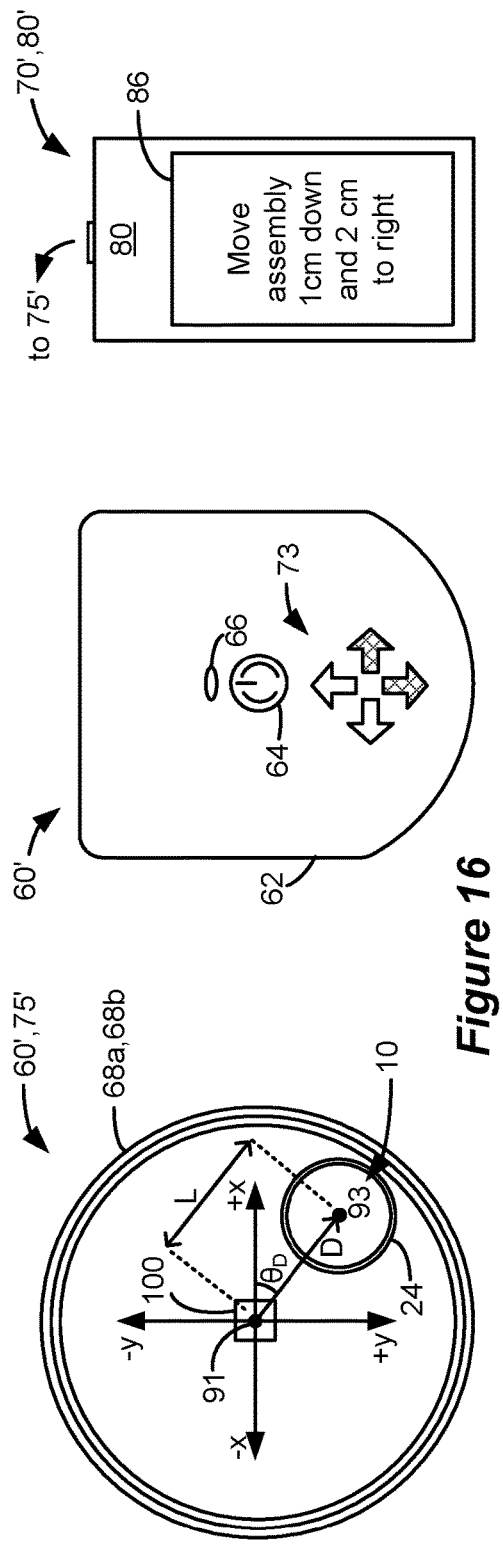
FIG. 16 shows use of vector D to determine and indicate the direction of lateral misalignment of the external charger to the IMD.

The external charger 60' or 70' may also use vector D alternatively or additionally to determine and indicate a direction of lateral misalignment. As shown in FIG. 16, the primary charging coil 68a/68b (e.g., its center 91) is significantly laterally shifted in position from the underlying IMD (e.g., its center 93), suggesting that indication of misalignment to the patient would be warranted. Further, because vector D is known, including its polar angle $\theta_D$, a lateral distance L and direction can be computed to indicate how the patient should move the primary charging coil 68a/68b so that it overlies the IMD—i.e., so that their centers 91 and 93 are collinear. In this regard, external charger 60' may have LEDs 73 as an example of alignment indicator 69 that illuminate the direction that the external charger 60' should be moved. External charger 70's charging controller 80' may also provide a directional alignment indicator, such as by displaying information regarding how to align the charging coil assembly 75' on the charging controller's screen 86. Such information may be textual as illustrated, or may comprise other graphics, such as an arrow with a particular length indicating the direction that the charging coil assembly 70' should be moved.

Figure 17:
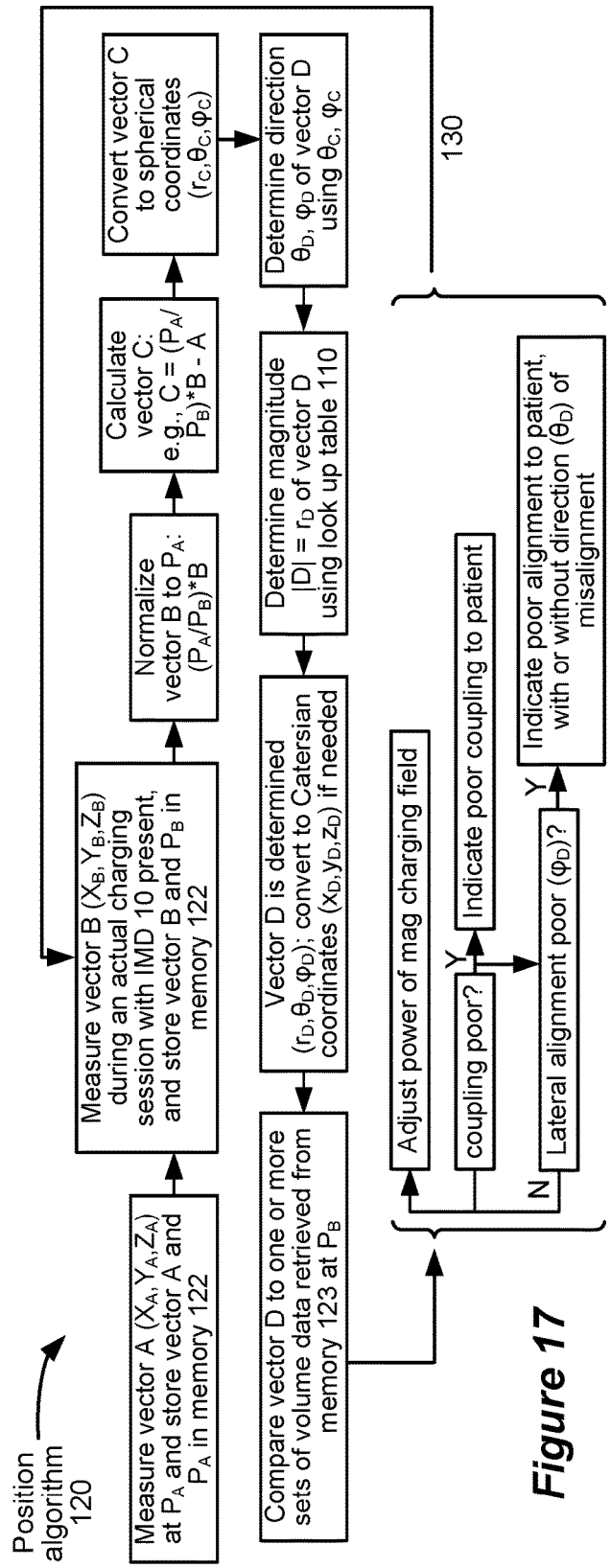
FIG. 17 shows the position algorithm in further detail.

FIG. 17 shows a flow chart explaining how the foregoing description can be implemented in the external charger 60' or 70' using a position algorithm 120 operable within the charger's control circuitry 61. Control circuitry 61 can comprise one or more microcontrollers programmed with firmware (such as the position algorithm 120), which microcontroller may for example comprise any of the STM32F4 ARM series of microcontrollers provided by STMicroeletronics, Inc., as described at http://www.st.com/content/st_com/en/products/microcontrollers/stm32-32-bit-arm-cortex-mcus/stm32f4-series.html?querycriteria=productId=SS1577. Control circuitry 61 may also comprise one or more of a microprocessor, FPGA, DSP, or other similar digital logic devices, and can comprise analog circuitry at least in part. Control circuitry 61 can further comprise a memory programmed with firmware and accessible to a microcontroller or other digital logic device should that logic device not contain suitable on-chip memory.

Much of position algorithm 120 as shown in FIG. 17 is by way of review of details set forth earlier. Not all steps of position algorithm 120 as illustrated are necessary to perform, and other steps could be added or changed.

Initialization vector A first is measured $(X_A, Y_A, Z_A)$ by the three-axis magnetic field sensor 100 when the IMD 10 is not present, and is stored in memory 122 along with a representation of the power $(P_A)$ of the magnetic charging field 65 used during vector A's measurement in memory 122. As noted earlier, this can take place at the external charger manufacturer prior to actual use of the external charger by the patient, such as by accessing a special test mode to which the patient may not have access.

Vector B is then measured $(X_B, Y_B, Z_B)$ during actual use to provide power to an IMD 10, and vector B is stored in memory 122 along with a representation of the power $(P_B)$ of the magnetic charging field 65 used during vector B's measurement in memory 122.

The magnitude of vector B is then normalized by the position algorithm 120 to that of initialization vector A, and a vector C $(X_C, Y_C, Z_C)$ is calculated by subtracting the two. Vector C represents the magnetic charging field reflected from the IMD 10. If helpful, vector C can be converted to spherical coordinates $(r_C, \theta_C, \varphi_C)$, which assists in determining vector D—a vector in physical space that points from the primary charging coil 68a/68b to the IMD. For example, the direction of vector D $(\theta_D, \varphi_D)$ can be determined directly from the direction of vector C $(\theta_C, \varphi_C)$, and these angles may be the same depending on how vector C was defined.

Next, position algorithm 120 determines the magnitude $|D|=r_D$ of vector D, preferably by using an empirically-determined look up table 110 stored in memory. The magnitude of vector $|C|$ and the azimuthal angle $\theta_D$ of vector D are particularly useful inputs to the table 110, as these parameters have significant effects on the magnitude of $|D|$.

Vector D in physical space has now been determined in spherical coordinates $(r_D, \theta_D, \varphi_D)$, and can be converted by position algorithm 120 to Cartesian coordinates $(x_D, y_D, z_D)$ if desired or convenient in subsequent steps.

Next, vector D is used by position algorithm 120 to assist in the charging process and to understand how well the external charger 60' or 70' (its primary charging coil 68a/68b) is coupled to the IMD 10. Position algorithm 120 next retrieves one or more sets of volume data from memory 123 associated with the current power of the magnetic charging field $P_B$. Vector D is compared to the one or more volumes to determine whether vector D point inside or outside of such volumes which indicates the degree of coupling to the IMD 10, as represented by the expected battery charging current in the IMD, Ibat, for example.

From this comparison, one or more different actions can be taken by the position algorithm 120. For example, the power of the magnetic charging field can be increased to provide more power to a poorly coupled implant, or can be reduced if the coupling is higher than needed to adequately power the IMD 10. If coupling is poor—for example, because vector D points outside of a particular volume data set (V1)—the poor coupling condition could be indicated to the patient via any of the examples of alignment indicators 69 discussed previously. Alternatively, the position algorithm 120 could inquire further as to the reason for the poor coupling, such as whether it is due to lateral misalignment or a deep implant. This is can be discerned by the position algorithm 120 by assessing azimuthal angle $\varphi_D$. If this angle is large, indicating poor alignment may be warranted, as lateral alignment of the charger 60' or charging coil assembly 75' is something a patient can address by moving the device 60' or 75'. If this angle is small, lateral misalignment may not be significant as the IMD 10 is simply deep, and the poor coupling may be addressed in other manners, such as by increasing the power of the magnetic charging field 65. Finally, if lateral misalignment is poor, the direction and distance L of this misalignment can be indicated to the patient (FIG. 16), with the position algorithm 120 using in particular the polar angle $\theta_D$ determined earlier.

As shown by arrow 130, position algorithm 120 can operate continually during a charging session on a reasonable time scale, such as every 0.5 seconds, with a new measured vector B being taken by the three-axis magnetic field sensor 100, new vectors C and D determined, etc.

Although particular embodiments have been shown and described, it should be understood that the above discussion is not intended to limit the present disclosure to these embodiments. It will be obvious to those skilled in the art that various changes and modifications may be made without departing from the spirit and scope of the present disclosure. Thus, the present disclosure is intended to cover alternatives, modifications, and equivalents that may fall within the spirit and scope of the claims.

What is claimed is:

1. An external charger configured to provide power to an implantable medical device (IMD), comprising:
    a charging coil configured when excited to provide a magnetic charging field;
    a three-axis magnetic field sensor within the charging coil; and
    control circuitry, wherein the control circuity is configured to determine a position of the IMD in three-dimensional space using measurements provided by the three-axis magnetic field sensor.

2. The external charger of claim 1, wherein the three-axis magnetic field sensor is located at a center of the charging coil.

3. The external charger of claim 1, further comprising a housing, wherein the charging coil, the three-axis magnetic field sensor, and the control circuitry are within the housing.

4. The external charger of claim 1, further comprising a housing, wherein the charging coil and three-axis magnetic field sensor are within the housing, and further comprising a charging controller coupled to the housing by a cable, wherein the control circuitry is within the charging controller.

5. The external charger of claim 1, wherein the three-axis magnetic field sensor comprises three orthogonally-oriented magnetic field sensors, and wherein the control circuitry is configured to determine the position of the IMD in three-dimensional space using measurements provided by each of the three orthogonal magnetic field sensors.

6. The external charger of claim 1, wherein the control circuitry is programmed with a position algorithm, and wherein the control circuitry is configured to determine the position of the IMD in three-dimensional space using the position algorithm.

7. The external charger of claim 6, wherein the position algorithm is configured to determine a first vector using the measurements provided by the three-axis magnetic field sensor when the charging coil is excited to provide the magnetic charging field but when the IMD is not proximate to the charging coil.

8. The external charger of claim 7, wherein the position algorithm is further configured to determine a second vector using the measurements provided by the three-axis magnetic field sensor when the charging coil is excited to provide the magnetic charging field and when the IMD is proximate to the charging coil.

9. The external charger of claim 8, wherein the position algorithm is further configured to compute a third vector from the first and second vectors.

10. The external charger of claim 9, wherein the first and second vectors are respectively measured at first and second powers of the magnetic charging field.

11. The external charger of claim 10, wherein the second vector is normalized to the first power before the third vector is computed from the first and second vectors.

12. The external charger of claim 9, wherein the position algorithm is further configured to compute a fourth vector from the third vector, wherein the fourth vector is indicative of the position of the IMD in three-dimensional space.

13. The external charger of claim 12, further comprising a look up table, wherein the control circuitry is configured to determine a magnitude of the fourth vector using a magnitude and azimuthal angle of the third vector.

14. The external charger of claim 1, wherein the control circuity is configured to determine a vector indicative of the position of the IMD in three-dimensional space.

15. The external charger of claim 14, further comprising one or more sets of volume data, wherein the control circuitry is further configured to compare the vector to the one or more sets of volume data to determine a coupling between the charging coil and the IMD.

16. The external charger of claim 15, wherein if the coupling between the charging coil and the IMD is determined to be low, the control circuitry is configured to increase a power of the magnetic charging field.

17. The external charger of claim 15, further comprising a user interface, wherein if the coupling between the charging coil and the IMD is determined to be low, the control circuitry is configured enable at least one indicator to indicate the low coupling condition to a patient via the user interface.

18. The external charger of claim 14, further comprising a user interface, wherein the control circuitry is configured to use the vector to indicate a direction indicative of lateral misalignment between the charging coil and the IMD.

* * * * *